US012734301B2

(12) United States Patent
Le Bail et al.

(10) Patent No.: US 12,734,301 B2
(45) Date of Patent: Sep. 15, 2026

(54) SYRINGE WITH HIGH PULL-OUT RESISTANCE

(71) Applicant: Laboratoires Vivacy, Paris (FR)

(72) Inventors: Noémie Le Bail, Copponex (FR); Philippe Goulinet, La Balme de Sillingy (FR)

(73) Assignee: Laboratoires Vivacy, Paris (FR)

(*) Notice: Subject to any disclaimer, the term of this patent is extended or adjusted under 35 U.S.C. 154(b) by 880 days.

(21) Appl. No.: 18/040,014

(22) PCT Filed: Jul. 23, 2021

(86) PCT No.: PCT/EP2021/070746

§ 371 (c)(1),
(2) Date: Jan. 31, 2023

(87) PCT Pub. No.: WO2022/023220

PCT Pub. Date: Feb. 3, 2022

(65) Prior Publication Data

US 2023/0330344 A1 Oct. 19, 2023

(30) Foreign Application Priority Data

Jul. 31, 2020 (FR) ....................................... 2008157

(51) Int. Cl.
*A61M 5/315* (2006.01)
*A61M 5/178* (2006.01)

(52) U.S. Cl.
CPC ........ *A61M 5/31515* (2013.01); *A61M 5/178* (2013.01); *A61M 5/315* (2013.01); *A61M 5/31511* (2013.01)

(58) Field of Classification Search
CPC .............. A61M 5/31515; A61M 5/315; A61M 5/31511; A61M 5/31501; A61M 2005/3151; A61M 2005/31523
See application file for complete search history.

(56) References Cited

U.S. PATENT DOCUMENTS 4,931,043 A 6/1990 Ray et al.
7,331,942 B2 2/2008 Alheidt et al.
(Continued)

FOREIGN PATENT DOCUMENTS

CN 1874815 A 12/2006
CN 101743025 A 6/2010
(Continued)

OTHER PUBLICATIONS

Chinese First Office Action for Chinese Application No. 202180053754.1, dated Dec. 5, 2025, 8 pages with English translation.
(Continued)

*Primary Examiner* — Tasnim Mehjabin Ahmed
(74) *Attorney, Agent, or Firm* — TraskBritt

(57) ABSTRACT

A syringe includes a syringe body that includes a stopper having an elastically deformable inner wall and delimiting a cavity. A piston is mounted so as to be able to slide inside the syringe body in an injection direction. The piston includes a rod. A pusher is arranged at a first end of the rod. A snap-fastening head is arranged at a second end of the rod and is snap-fastened inside the cavity of the stopper. The snap-fastening head has a planar bearing surface bearing against the inner wall of the stopper when the piston slides in the direction opposite to the injection direction. The snap-fastening head includes at least one protruding element that protrudes from the planar bearing surface and that is arranged to penetrate the inner wall of the stopper when the piston slides in the direction opposite to the injection direction.

19 Claims, 6 Drawing Sheets

(56) References Cited

U.S. PATENT DOCUMENTS

| | | | | |
|---|---|---|---|---|
| 8,475,415 | B2 | 7/2013 | Schiller et al. | |
| 9,289,557 | B2 | 3/2016 | Ivosevic et al. | |
| 11,291,772 | B2 | 4/2022 | Bogert et al. | |
| 2003/0120219 | A1 | 6/2003 | Nielsen et al. | |
| 2010/0167231 | A1* | 7/2010 | Dubbe | A61C 5/62 222/386 |
| 2011/0034882 | A1 | 2/2011 | Quinn et al. | |
| 2012/0136298 | A1 | 5/2012 | Bendix et al. | |
| 2012/0259288 | A1 | 10/2012 | Wagner et al. | |

FOREIGN PATENT DOCUMENTS

| | | | |
|---|---|---|---|
| CN | 102458521 | A | 5/2012 |
| CN | 109289104 | A | 2/2019 |
| CN | 110312541 | A | 10/2019 |
| EP | 0354368 | A2 | 2/1990 |
| KR | 10-2009-0035706 | A | 4/2009 |
| WO | 03/047668 | A1 | 6/2003 |
| WO | 2008/064283 | A2 | 5/2008 |
| WO | 2011/023738 | A1 | 3/2011 |

OTHER PUBLICATIONS

Chinese Search Report for Chinese Application No. 202180053754.1, dated Dec. 5, 2025, 5 pages with English translation.

European Communication pursuant to Article 94(3) EPC for European Application No. 21751527.9, dated Dec. 9, 2024, 12 pages with English machine translation.

European Communication pursuant to Article 94(3) EPC for European Application No. 21751527.9, dated Jun. 12, 2025, 15 pages with English machine translation.

Korean Written Opinion for Korean Application No. 10-2023-7006505, dated Mar. 12, 2026, 14 pages with English translation.

International Search Report for International Application No. PCT/EP2021/070746, mailed Oct. 28, 2021, 6 pages with English translation.

International Written Opinion for International Application No. PCT/EP2021/070746, mailed Oct. 28, 2021, 11 pages with English machine translation.

* cited by examiner

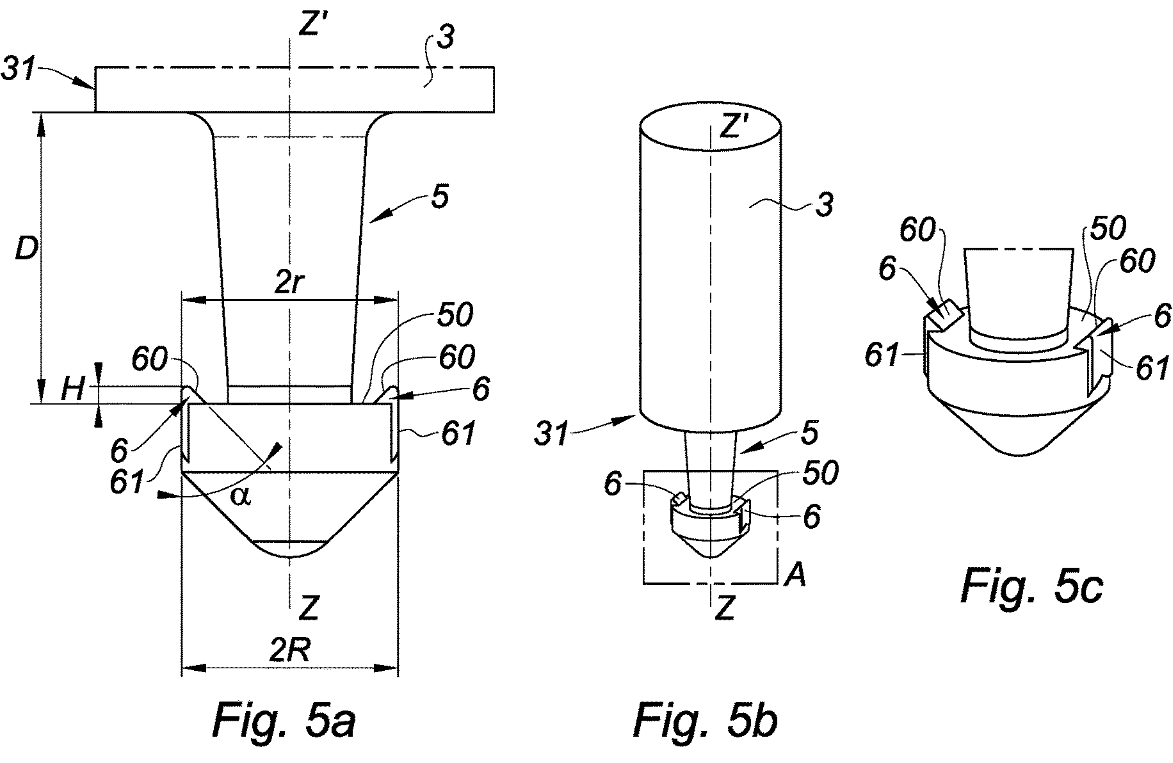
Fig. 5a
Fig. 5b
Fig. 5c
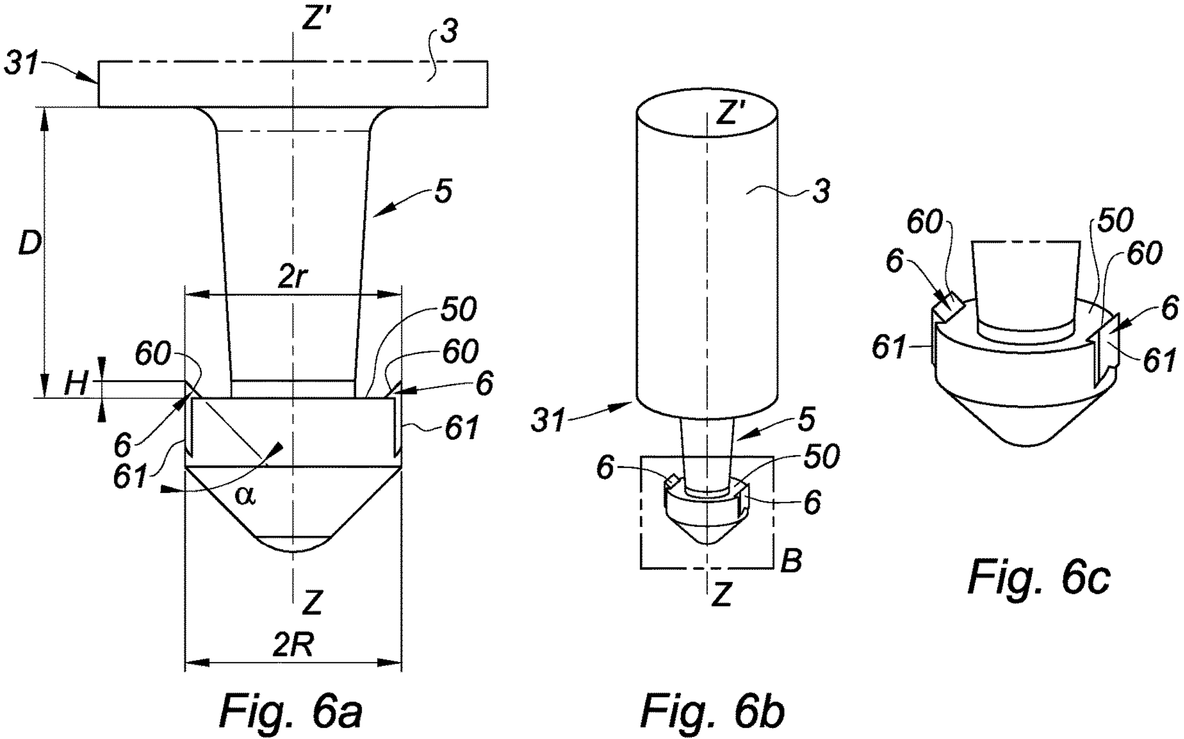
Fig. 6a
Fig. 6b
Fig. 6c

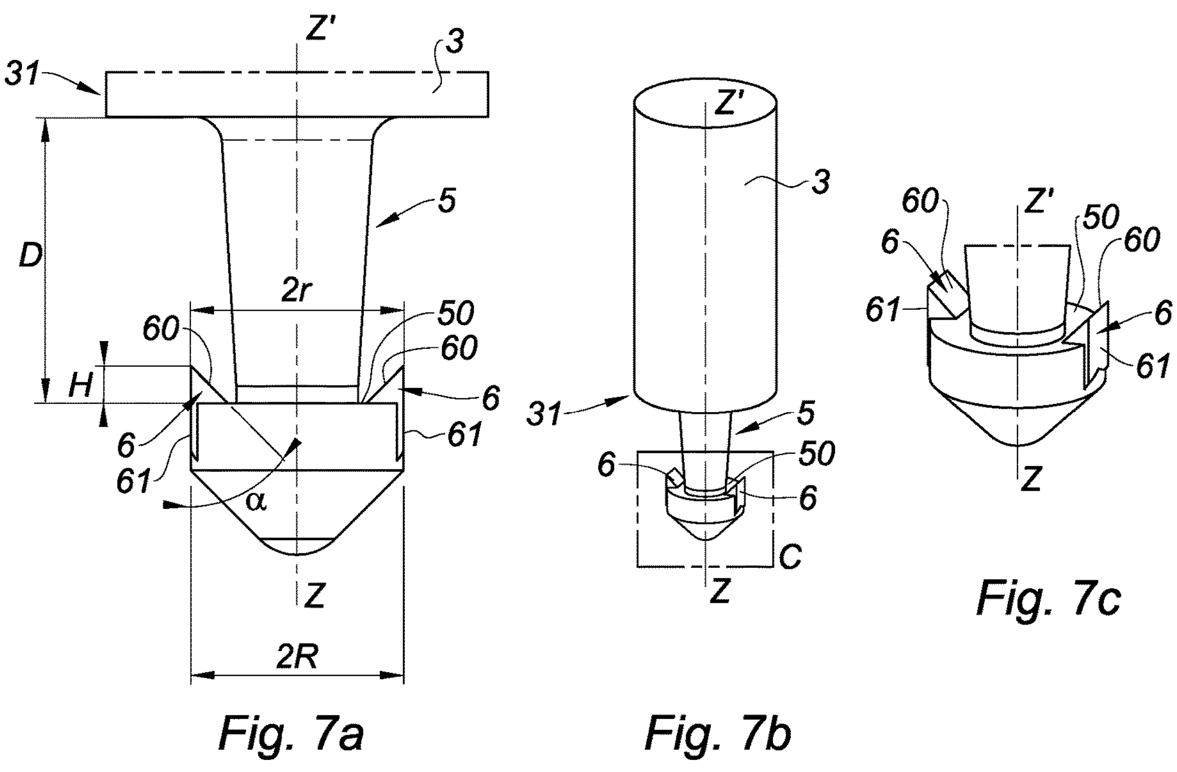
Fig. 7a
Fig. 7b
Fig. 7c
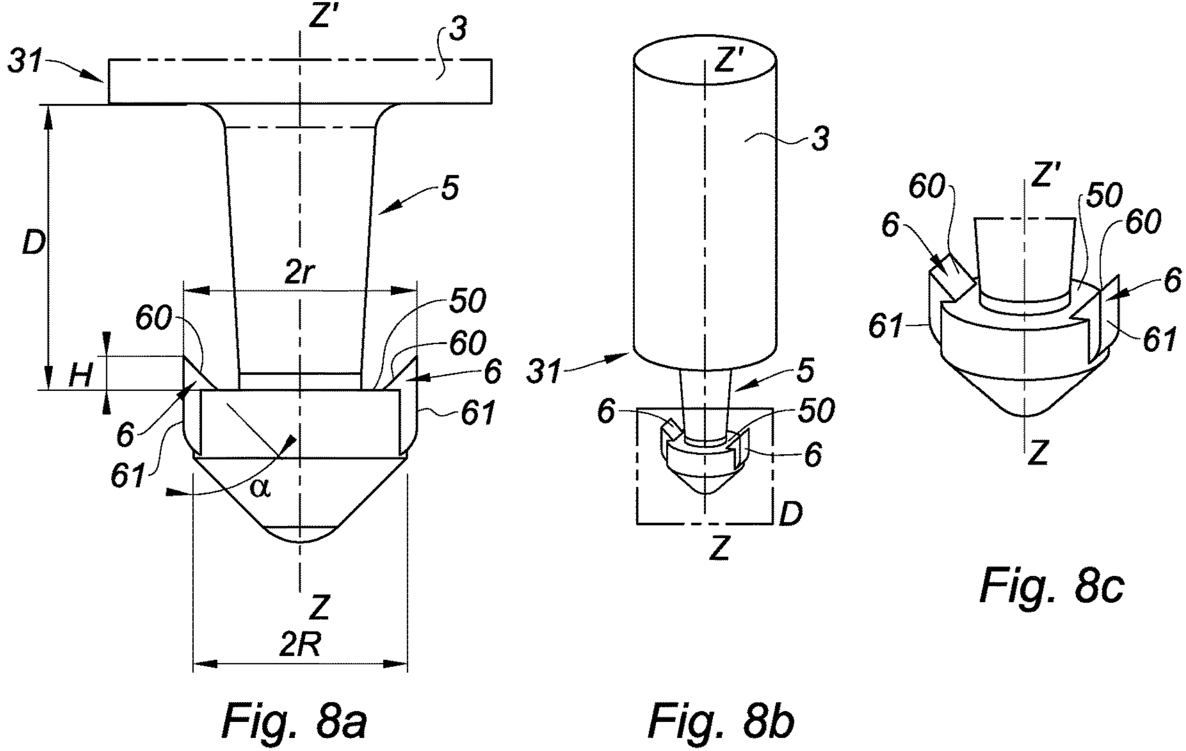
Fig. 8a
Fig. 8b
Fig. 8c

SYRINGE WITH HIGH PULL-OUT RESISTANCE

CROSS-REFERENCE TO RELATED APPLICATIONS

This application is a national phase entry under 35 U.S.C. § 371 of International Patent Application PCT/EP2021/070746, filed Jul. 23, 2021, designating the United States of America and published as International Patent Publication WO 2022/023220 A1 on Feb. 3, 2022, which claims the benefit under Article 8 of the Patent Cooperation Treaty to French Patent Application Serial No. FR2008157, filed Jul. 31, 2020.

TECHNICAL FIELD

The disclosure relates to the technical field of syringes.

The disclosure notably finds an application in the injection of viscoelastic gels based on hyaluronic acid, in the field of anti-aging procedures and medical esthetics.

BACKGROUND

A syringe known from the prior art comprises:

- a syringe body that is intended to receive a product for injection and that comprises a stopper; the stopper having an elastically deformable inner wall and delimiting a cavity; the syringe body being intended to be equipped with a needle holder;
- a piston that is mounted so as to be able to slide inside the syringe body in an injection direction of the product and in an opposite direction and that comprises a rod having a first end and an opposite second end;
- a pusher that is arranged at the first end of the rod; and
- a snap-fastening head that is arranged at the second end of the rod and that is snap-fastened inside the cavity of the stopper; the snap-fastening head having a planar bearing surface bearing against the inner wall of the stopper when the piston slides in the direction opposite to the injection direction of the product.

The term "physician" will be used below, it being understood that the term designates any user of the syringe.

Such a syringe from the prior art is not entirely satisfactory insofar as the snap-fastening head is liable to be removed from the cavity of the stopper when the physician wishes to check that the needle is not in a patient's vein, in the context of an application by intradermal injection. To that end, the physician performs an aspiration by pulling on the pusher, in the direction opposite to the injection direction of the product, over a distance conventionally of between 5 mm and 10 mm, and this is done to check the absence of a reflux of blood. This checking maneuver by the physician is an important precaution since any injection below the dermal level considerably increases the risk of intravascular injection. This checking maneuver by the physician leads to the exertion of a significant force-referred to as pull-out force-(for example, of the order of 6 to 8 N) on the connection between the planar bearing surface of the snap-fastening head and the inner wall of the stopper, particularly when the product for injection is viscous (suction effect). Such an intensity of force, being exerted on the connection between the planar bearing surface of the snap-fastening head and the inner wall of the stopper, may cause such a significant deformation of the inner wall of the stopper that the snap-fastening head may then be removed from the cavity of the stopper, as illustrated in FIG. 1.

Those skilled in the art are therefore searching for a syringe that makes it possible to withstand a high pull-out force, for example, of greater than or equal to 9 N, in order to make the checking maneuver by the physician safer.

BRIEF SUMMARY

Embodiments of the disclosure aim to completely or partially remedy the aforementioned drawbacks. To this end, a subject of the disclosure is a syringe, comprising:

- a syringe body that is intended to receive a product for injection and that comprises a stopper; the stopper having an elastically deformable inner wall and delimiting a cavity;
- a piston that is mounted so as to be able to slide inside the syringe body in an injection direction of the product and in an opposite direction and that comprises a rod having a first end and an opposite second end;
- a pusher that is arranged at the first end of the rod; and
- a snap-fastening head that is arranged at the second end of the rod and that is snap-fastened inside the cavity of the stopper; the snap-fastening head having a planar bearing surface bearing against the inner wall of the stopper when the piston slides in the direction opposite to the injection direction of the product;
- notable in that the snap-fastening head comprises at least one protruding element that protrudes from the planar bearing surface and that is arranged so as to penetrate the inner wall of the stopper when the piston slides in the direction opposite to the injection direction of the product.

Definitions

"Inner wall" is understood to mean the inner surface of the stopper that delimits a cavity, the stopper being hollow.

"Elastically deformable" is understood to mean that the inner wall of the stopper can deform in a reversible manner under the action of mechanical stresses (lower than the elastic limit), that is to say that the inner wall of the stopper can return to its initial shape when the mechanical stresses cease.

"Snap-fastening" is understood to mean an elastic engagement between the snap-fastening head and the inner wall of the stopper, inside the cavity of the stopper.

"Protruding" is understood to mean that the element goes beyond the planar bearing surface so as to extend in a half-space defined by the planar bearing surface, the half-space extending toward the second end of the rod.

Thus, such a syringe according to embodiments of the disclosure makes it possible to withstand a greater pull-out force than in the prior art, and this is due to the protruding element or protruding elements that anchor themselves in the inner wall of the stopper (by locally deforming said wall) when the piston slides in the direction opposite to the injection direction of the product, in particular during the execution of the checking maneuver by the physician, as illustrated in FIG. 2.

The syringe according to embodiments of the disclosure may comprise one or more of the following features.

According to one feature of embodiments of the disclosure, the or each protruding element comprises two planar surfaces forming an acute dihedral angle, preferably of between 10° and 80°, more preferably of between 30° and 60°, even more preferably of between 40° and 50°.

"Acute dihedral angle" is understood to mean the angle between two planes defined by the two planar surfaces, of between 0° and 90°.

Thus, an advantage obtained by such planar surfaces is the formation of a pointed part that allows the protruding element to penetrate the inner wall of the stopper when the piston slides in the direction opposite to the injection direction of the product, so as to anchor itself there by locally deforming said wall. In other words, such planar surfaces form an anchoring point.

According to one feature of embodiments of the disclosure, the two planar surfaces of the or of each protruding element are joined together so as to form an edge.

"To form an edge" is understood to mean the formation of a line of intersection between the two planar surfaces. In other words, the two planar surfaces of the or of each protruding element are joined together so as to form a sharp edge.

Thus, an advantage obtained is that the penetration of the inner wall of the stopper by the protruding element is facilitated.

According to one feature of embodiments of the disclosure, the or each protruding element comprises a conical or frustoconical surface exhibiting an acute cone angle, preferably of between 10° and 80°, more preferably of between 30° and 60°, even more preferably of between 40° and 50°.

"Conical surface" is understood to mean the surface created by a segment (generatrix) passing through a fixed point (apex) and through a variable point describing a curve (directrix). By way of non-limiting examples, the directrix curve may be a circle, an ellipse or a polygon.

"Frustoconical surface" is understood to mean a part of the conical surface between the base and a planar section parallel to the base.

"Acute cone angle" is understood to mean the half-angle at the apex of the cone, of between 0° and 90°.

Thus, an advantage obtained by such a conical or frustoconical surface is the formation of a pointed part that allows the protruding element to penetrate the inner wall of the stopper when the piston slides in the direction opposite to the injection direction of the product, so as to anchor itself there by locally deforming said wall. In other words, such a conical or frustoconical surface forms an anchoring point.

According to one feature of embodiments of the disclosure, the or each protruding element forms a tooth exhibiting an acute tip angle, preferably of between 10° and 80°, more preferably of between 30° and 60°, even more preferably of between 40° and 50°.

"Tooth" is understood to mean two flanks joined together so as to form a crest surface.

"Acute tip angle" is understood to mean the dihedral angle formed between the two flanks of the tooth, the dihedral angle being between 0° and 90°.

Thus, an advantage obtained by such a tooth is the formation of a pointed part that allows the protruding element to penetrate the inner wall of the stopper when the piston slides in the direction opposite to the injection direction of the product, so as to anchor itself there by locally deforming said wall. In other words, such a tooth forms an anchoring point.

According to one feature of embodiments of the disclosure, the planar bearing surface is situated at a distance, denoted D, from the second end of the rod, and the or each protruding element has a height, denoted H, along the normal to the planar bearing surface, such that:

$$0.05\ D \leq H \leq 0.2\ D,\ \text{preferably}\ 0.06\ D \leq H \leq 0.18\ D.$$

Thus, an advantage obtained is that a penetration depth of the protruding element into the inner wall of the stopper is obtained that permits sufficient anchorage to withstand a high pull-out force (for example, of greater than or equal to 9 N), while still maintaining a snap-fastening force that is not too high (for example, of less than 8 N) in order for the snap-fastening head to engage with the inner wall of the stopper inside the cavity of the stopper.

According to one feature of embodiments of the disclosure, the syringe comprises a set of protruding elements that protrude from the planar bearing surface and that are arranged so as to penetrate the inner wall of the stopper when the piston slides in the direction opposite to the injection direction of the product.

Thus, an advantage obtained is that the resistance to the pull-out force is increased by increasing the number of protruding elements.

According to one feature of embodiments of the disclosure, the protruding elements of the set form patterns that are spaced apart periodically on the planar bearing surface.

"Spaced apart periodically" is understood to mean that the patterns repeat (preferably in an identical manner) according to a given interval, that is to say according to a given spatial period.

Thus, an advantage obtained is that the adhesion of the protruding elements to the inner wall of the stopper is increased (knurling effect), and thus the resistance to the pull-out force is increased.

According to one feature of embodiments of the disclosure, the planar bearing surface is circular, and the set of protruding elements is distributed uniformly around the planar bearing surface.

"Distributed uniformly" is understood to mean that the protruding elements of the set are arranged at an invariable radial distance with respect to the center of the circular planar surface, and are distributed around the planar bearing surface according to a uniform law so as to form an angle of $2\pi/N$ radians, where N is the number of protruding elements in the set.

Thus, an advantage obtained by such a geometry is that the resistance to the pull-out force is increased.

According to one feature of embodiments of the disclosure, the snap-fastening head extends along a longitudinal axis, and the protruding elements of the set exhibit axial symmetry with respect to the longitudinal axis.

Thus, an advantage obtained by such a geometry is that the resistance to the pull-out force is increased.

According to one feature of embodiments of the disclosure, the planar bearing surface has a radius, denoted R, and the or each protruding element has a lateral end situated at a radial distance, denoted r, such that:

$$0.8\ R \leq r \leq 1.20\ R,\ \text{preferably}\ R \leq r \leq 1.16\ R.$$

"Radial distance" is understood to mean the distance from the lateral end with respect to the center of the planar bearing surface.

Thus, an advantage obtained is that the snap-fastening force required for engagement of the snap-fastening head with the inner wall of the stopper inside the cavity of the stopper is limited, while reducing the risks of the lateral ends of the protruding elements breaking during the snap-fastening.

According to one feature of embodiments of the disclosure, the or each protruding element and the snap-fastening head are in one piece.

Thus, an advantage obtained is that their manufacture is facilitated, which may be carried out by molding.

According to one feature of embodiments of the disclosure, the snap-fastening head and the protruding element or elements are made of a plastics material, preferably a thermoplastic, more preferably polycarbonate.

According to one feature of embodiments of the disclosure, the stopper is made of an elastomeric material, preferably a chlorinated or brominated butyl rubber.

According to one feature of embodiments of the disclosure, the inner wall of the stopper comprises at least one shoulder against which the planar bearing surface of the snap-fastening head bears when the piston slides in the direction opposite to the injection direction of the product; and the protruding element or elements are arranged so as to penetrate the shoulder when the piston slides in the direction opposite to the injection direction of the product.

Thus, an advantage obtained by the shoulder is the formation of a support for the snap-fastening head when the piston slides in the direction opposite to the injection direction of the product.

BRIEF DESCRIPTION OF THE DRAWINGS

Other features and advantages will become apparent from the detailed description of various embodiments of the disclosure, the description containing examples and references to the appended drawings.

FIGS. 5*a* to 5*c* are schematic views (in section on an enlarged scale, in perspective and in perspective on an enlarged scale, respectively) of a snap-fastening head equipping a syringe according to embodiments of the disclosure, illustrating a first embodiment of the protruding elements. FIG. 5*c* is a perspective view on an enlarged scale of zone A in FIG. 5*b*.

FIGS. 6*a* to 6*c* are schematic views (in section on an enlarged scale, in perspective and in perspective on an enlarged scale, respectively) of a snap-fastening head equipping a syringe according to embodiments of the disclosure, illustrating a second embodiment of the protruding elements. FIG. 6*c* is a perspective view on an enlarged scale of zone B in FIG. 6*b*.

FIGS. 7*a* to 7*c* are schematic views (in section on an enlarged scale, in perspective and in perspective on an enlarged scale, respectively) of a snap-fastening head equipping a syringe according to embodiments of the disclosure, illustrating a third embodiment of the protruding elements. FIG. 7*c* is a perspective view on an enlarged scale of zone C in FIG. 7*b*.

FIGS. 8*a* to 8*c* are schematic views (in section on an enlarged scale, in perspective and in perspective on an enlarged scale, respectively) of a snap-fastening head equipping a syringe according to embodiments of the disclosure, illustrating a fourth embodiment of the protruding elements. FIG. 8*c* is a perspective view on an enlarged scale of zone D in FIG. 8*b*.

FIG. 9*c* is a perspective view on an enlarged scale of zone E in FIG. 9*b*.

FIG. 10*c* is a perspective view on an enlarged scale of zone F in FIG. 10*b*.

Figure 1:
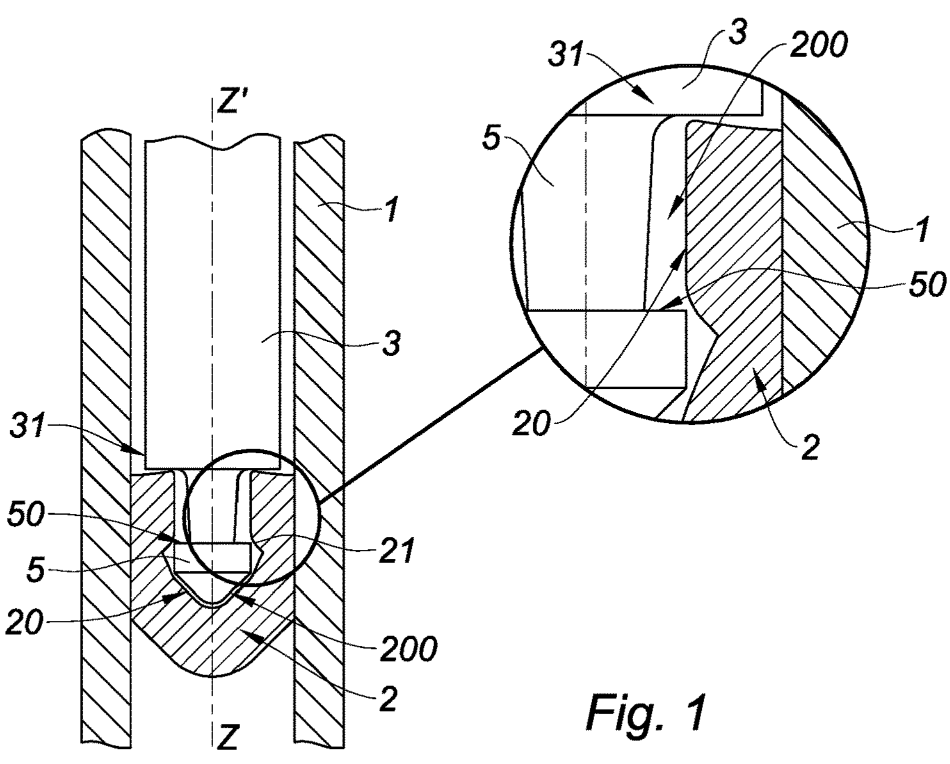
FIG. 1 is a partial schematic view, in section, of a syringe according to the prior art, in which the inset illustrates a significant deformation of the inner wall of the stopper, the snap-fastening head then being able to be removed from the cavity of the stopper when the pull-out force is high.
Figure 2:
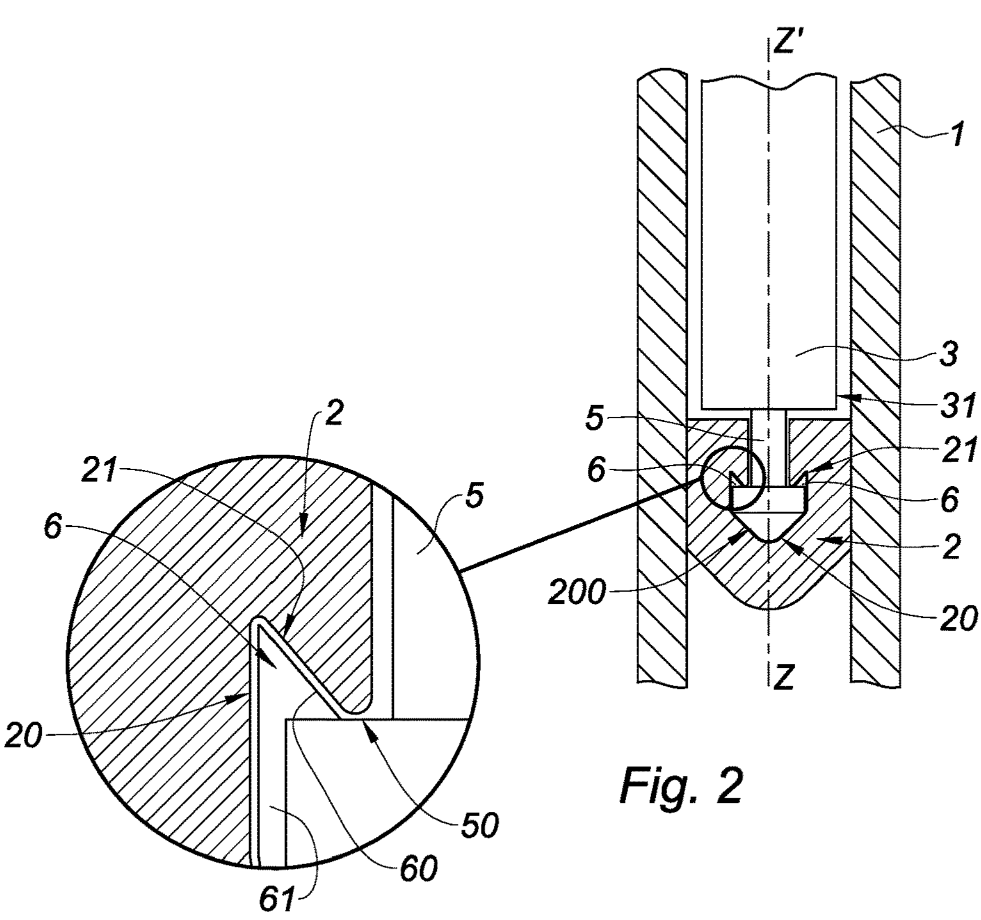
FIG. 2 is a partial schematic view, in section, of a syringe according to embodiments of the disclosure, in which the inset illustrates a protruding element that anchors itself in the inner wall of the stopper (by locally deforming said wall) when the piston slides in the direction opposite to the injection direction of the product.
Figure 3:
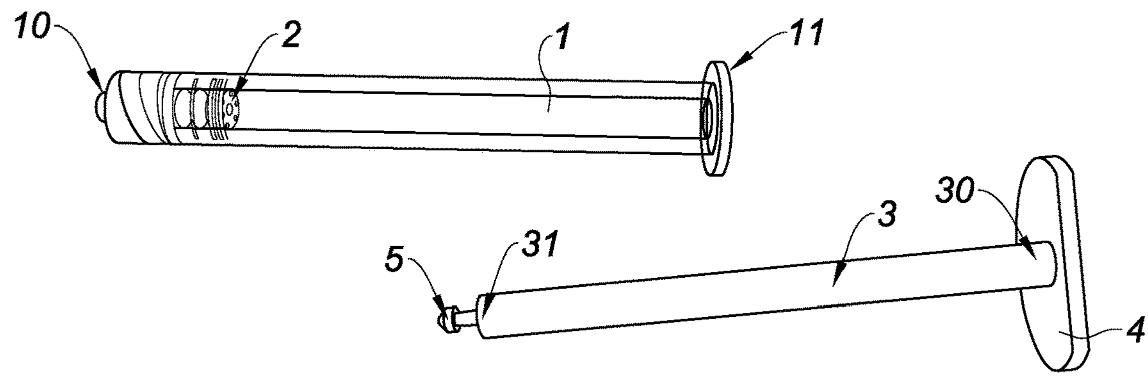
FIG. 3 is a schematic view, in perspective, of a syringe according to embodiments of the disclosure, separately illustrating the syringe body provided with a stopper and the piston provided with a snap-fastening head (the protruding elements are not clearly visible on account of their dimensions).
Figure 4A:
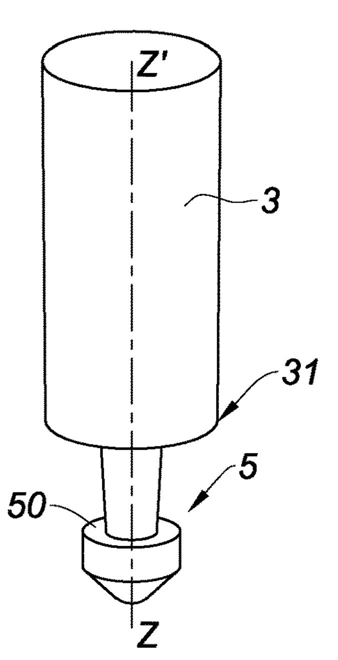
FIGS. 4*a* to 4*c* are schematic views (in perspective, in section and on an enlarged scale, respectively) of a snap-fastening head equipping a syringe from the prior art.
Figure 4B:
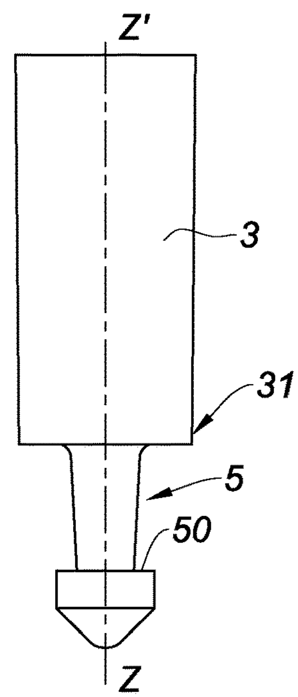
Figure 4C:
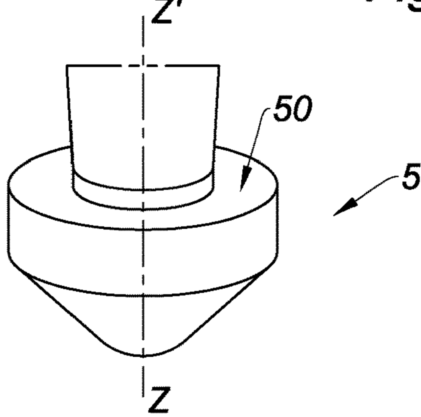

It should be noted that, for the sake of legibility and ease of understanding, the drawings described above are schematic, and are not necessarily to scale. The sections are effected along the longitudinal axis of the rod.

DETAILED DESCRIPTION

For the sake of simplicity, elements that are identical or that perform the same function in the various embodiments have been designated with the same references.

A subject of the disclosure is a syringe, comprising:

- a syringe body 1 that is intended to receive a product for injection and that comprises a stopper 2; the stopper 2 having an elastically deformable inner wall 20 and delimiting a cavity 200;
- a piston that is mounted so as to be able to slide inside the syringe body in an injection direction of the product and in an opposite direction and that comprises a rod 3 having a first end 30 and an opposite second end 31;
- a pusher 4 that is arranged at the first end 30 of the rod 3; and
- a snap-fastening head 5 that is arranged at the second end 31 of the rod 3 and that is snap-fastened inside the cavity 200 of the stopper 2, the snap-fastening head 5 having a planar bearing surface 50 bearing against the inner wall 20 of the stopper 2 when the piston slides in the direction opposite to the injection direction of the product;
- notable in that the snap-fastening head 5 comprises at least one protruding element 6 that protrudes from the planar bearing surface 50 and that is arranged so as to penetrate the inner wall 20 of the stopper 2 when the piston slides in the direction opposite to the injection direction of the product.

Different forms and different arrangements of the protruding element or elements are illustrated in FIGS. 5*a* to 5*c*, 6*a* to 6*c*, 7*a* to 7*c*, 8*a* to 8*c*, 9*a* to 9*c* and 10*a* to 10*c*.

Syringe Body

The syringe body 1 has:

a first end 10 that is intended to be equipped with a needle holder; and a second, opposite end 11.

The first and second ends 10, 11 of the syringe body 1 are open. The first end 10 of the syringe body 1 is open so as to receive a needle holder. In the absence of a needle holder, the first end 10 of the syringe body 1 may be blocked by a cap. The second end 11 of the syringe body 1 is open so as to receive the piston. The syringe advantageously comprises gripping wings that are arranged at the second end 11 of the syringe body 1.

The syringe body 1 is preferably cylindrical. The syringe body 1 is preferably made of a plastics material, more preferably a thermoplastic material. By way of non-limiting example, the syringe body 1 may be made of polycarbonate.

By way of non-limiting example, the product for injection may be a viscoelastic gel based on hyaluronic acid.

Stopper

The inner wall 20 of the stopper 2 advantageously comprises at least one shoulder 21 against which the planar bearing surface 50 of the snap-fastening head 5 bears when the piston slides in the direction opposite to the injection direction of the product.

When the snap-fastening head 5 is snap-fastened inside the cavity 200 of the stopper 2, the stopper 2 forms a piston head. By way of non-limiting example, when the stopper 2 is in an end-of-travel position, the rod 3 may protrude from the syringe body 1 over a distance of between 20 mm and 30 mm.

The stopper 2 is advantageously made of an elastomeric material, preferably a chlorinated or brominated butyl rubber. The stopper 2 is made of a soft material, advantageously having a hardness of between 45 Shore A and 60 Shore A.

Piston Rod

The rod 3 is preferably made of a plastics material, more preferably a thermoplastic material. By way of non-limiting example, the rod 3 may be made of polycarbonate. The rod 3 extends along a longitudinal axis Z'-Z.

Pusher

The pusher 4 and the rod 3 may be in one piece. The pusher 4 advantageously has a mass of less than or equal to 10 grams in order to not unnecessarily weigh down the syringe.

Snap-Fastening Head

The planar bearing surface 50 is situated at a distance, denoted D, from the second end 31 of the rod 3. By way of non-limiting example, the distance D may be between 3 mm and 4 mm, preferably between 3.2 mm and 3.6 mm. The planar bearing surface 50 may be circular, and have a radius, denoted R. By way of non-limiting example, the radius R may be between 1 mm and 1.5 mm.

The snap-fastening head 5 extends along the longitudinal axis Z'-Z.

The or each protruding element 6 and the snap-fastening head 5 are advantageously in one piece, and preferably obtained by molding. The snap-fastening head 5 and the protruding element or elements 6 are advantageously made of a plastics material, preferably a thermoplastic, more preferably polycarbonate. The snap-fastening head 5 and the protruding element or elements 6 are made of a hard material, advantageously having a hardness of between 60 Shore D and 90 Shore D.

Form of the Protruding Element or Elements

According to one embodiment, the or each protruding element 6 comprises two planar surfaces 60, 61 forming an acute dihedral angle $\alpha$, preferably of between 10° and 80°, more preferably of between 30° and 60°, even more preferably of between 40° and 50°. As illustrated in FIGS. 6*a* to 6*c*, 7*a* to 7*c*, 8*a* to 8*c* and 9*a* to 9*c*, the two planar surfaces 60, 61 of the or of each protruding element 6 may be joined together so as to form an edge, that is to say a sharp edge. According to one alternative illustrated in FIGS. 5*a* to 5*c* and 10*a* to 10*c*, the two planar surfaces 60, 61 of the or of each protruding element 6 may be joined together so as to form a rounded edge. The (real or virtual) line of intersection of the dihedral angle $\alpha$ is oriented on the side of the rod 3.

According to one embodiment that is not illustrated, the or each protruding element 6 comprises a conical or frustoconical surface exhibiting an acute cone angle, preferably of between 10° and 80°, more preferably of between 30° and 60°, even more preferably of between 40° and 50°. The (real or virtual) apex of the cone of the conical or frustoconical surface is oriented on the side of the rod 3.

According to one embodiment that is not illustrated, the or each protruding element 6 forms a tooth exhibiting an acute tip angle, preferably of between 10° and 80°, more preferably of between 30° and 60°, even more preferably of between 40° and 50°. The crest surface of the tooth is oriented on the side of the rod 3.

Arrangement of the Protruding Element or Elements

The or each protruding element 6 has a height, denoted H, along the normal to the planar bearing surface 50 such that advantageously:

$$0.05\ D \le H \le 0.2\ D,\ \text{preferably}\ 0.06\ D \le H \le 0.18\ D.$$

When the planar bearing surface 50 of the snap-fastening head 5 is circular, the or each protruding element 6 has a lateral end situated at a radial distance, denoted r, such that:

$$0.8\ R \le r \le 1.20\ R,\ \text{preferably}\ R \le r \le 1.16\ R.$$

The syringe may comprise a set of protruding elements 6 that protrude from the planar bearing surface 50 and that are arranged so as to penetrate the inner wall 20 of the stopper 2 when the piston slides in the direction opposite to the injection direction of the product.

According to one embodiment that is not illustrated, the protruding elements 6 of the set may form patterns that are spaced apart periodically on the planar bearing surface 50. By way of non-limiting example, the patterns may be arranged on the planar bearing surface 50 so as to delimit radial striations and form a knurled structure.

When the planar bearing surface 50 is circular, the set of protruding elements 6 is advantageously distributed uniformly around the planar bearing surface 50. It is possible to have an even number or an odd number of protruding elements 6 distributed uniformly around the planar bearing surface 50.

The protruding elements 6 of the set advantageously exhibit axial symmetry with respect to the longitudinal axis Z'-Z of the snap-fastening head 5.

If the inner wall 20 of the stopper 2 comprises at least one shoulder 21 against which the planar bearing surface 50 of the snap-fastening head 5 bears when the piston slides in the direction opposite to the injection direction of the product, the protruding element or elements 6 are then advantageously arranged so as to penetrate the shoulder 21 when the piston slides in the direction opposite to the injection direction of the product.

Figures 9A, 9B, 9C, 10A, 10B, 10C:
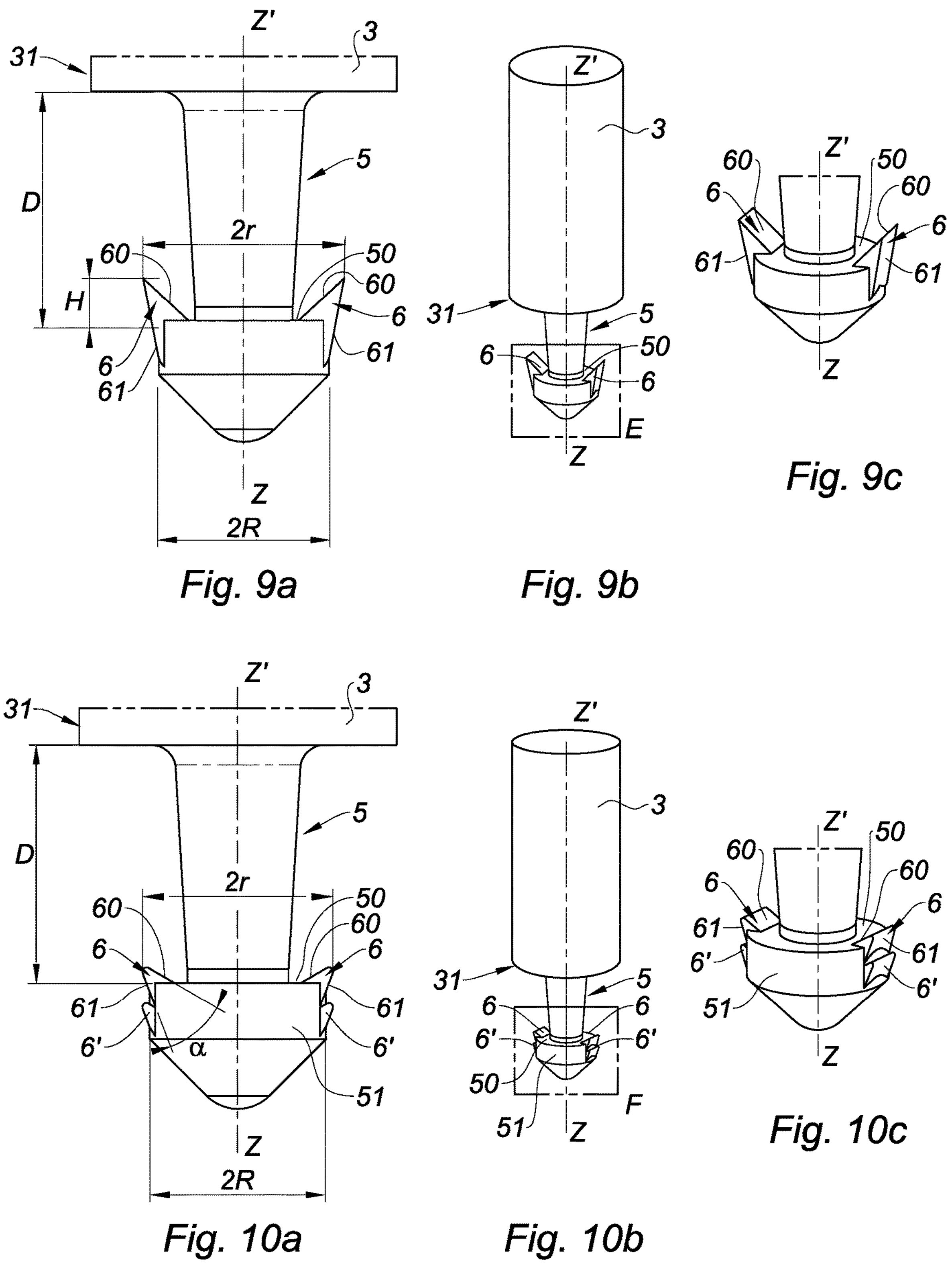
FIGS. 9*a* to 9*c* are schematic views (in section on an enlarged scale, in perspective and in perspective on an enlarged scale, respectively) of a snap-fastening head equipping a syringe according to embodiments of the disclosure, illustrating a fifth embodiment of the protruding elements.
FIGS. 10*a* to 10*c* are schematic views (in section on an enlarged scale, in perspective and in perspective on an enlarged scale, respectively) of a snap-fastening head equipping a syringe according to embodiments of the disclosure, illustrating a sixth embodiment of the protruding elements.

As illustrated in FIGS. 10*a* to 10*c*, the snap-fastening head 5 may comprise at least one additional protruding element 6' that protrudes from a lateral border 51 of the snap-fastening head 5 and that is arranged so as to penetrate the inner wall 20 of the stopper 2 when the piston slides in the direction opposite to the injection direction of the product.

Test Benches

Figure 11:
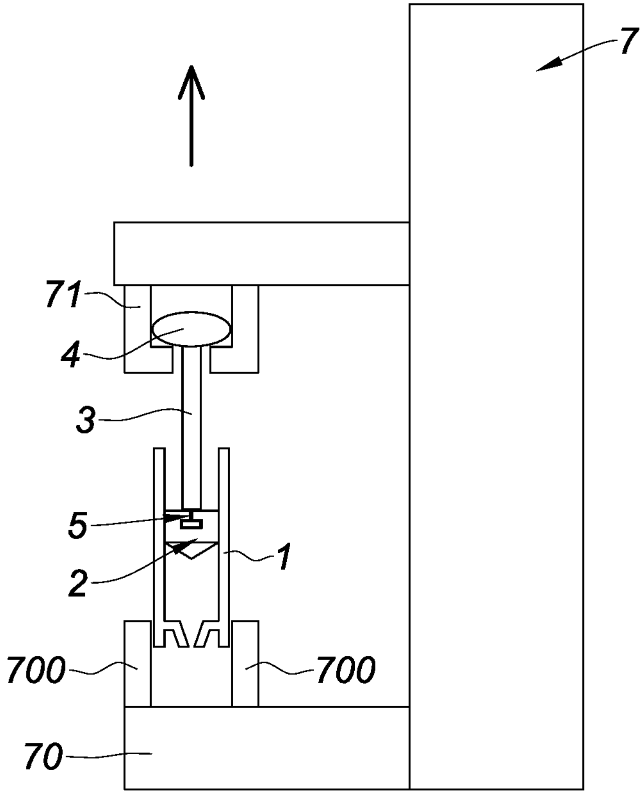
FIG. 11 is a synoptic diagram (in section) of a test bench for measuring the pull-out force that makes it possible to remove the snap-fastening head from the inner wall of the stopper.

The test bench 7 schematically illustrated in FIG. 11 makes it possible to measure the pull-out force for removing the snap-fastening head 5 from the inner wall 20 of the stopper 2. The test bench 7 comprises a baseplate 70 comprising walls 700 that form a jaw and that are arranged so as to maintain the position of the syringe by enclosing it. The stopper 2 is fastened to the syringe body 1 (for example, at the first end 10 of the syringe body 1), preferably with the aid of a strong adhesive. The test bench 7 comprises an actuator 71 arranged so as to pull the pusher 4 (tractive movement) until the snap-fastening head 5 is pulled out of the stopper 2. The actuator 71 is configured to move at a speed representative of the speed of execution of the checking maneuver by the physician, over a predetermined distance. The load generated by the actuator 71 is measured by a sensor during the tractive movement. The maximum value of the load generated by the actuator 71 is retained as the pull-out force value.

Figure 12:
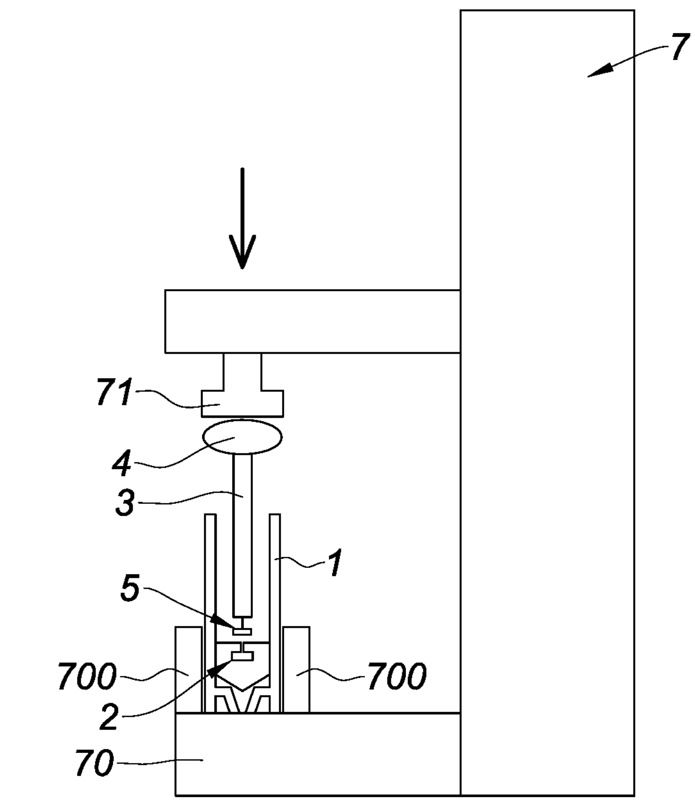
FIG. 12 is a synoptic diagram (in section) of a test bench for measuring the snap-fastening force required for engagement of the snap-fastening head inside the cavity of the stopper.

The test bench 7 schematically illustrated in FIG. 12 makes it possible to measure the snap-fastening force required for engagement of the snap-fastening head 5 inside the cavity 200 of the stopper 2. The test bench 7 comprises a baseplate 70 comprising walls 700 that form a jaw and that are arranged so as to maintain the position of the syringe by enclosing it. The stopper 2 is introduced as far as the bottom of the syringe body 1 (at the first end 10 of the syringe body 1). The test bench 7 comprises an actuator 71 arranged so as to push the pusher 4 (compressive movement) until the snap-fastening head 5 is snap-fastened inside the cavity 200 of the stopper 2. The load generated by the actuator 71 is measured by a sensor during the compressive movement. The snap-fastening of the snap-fastening head 5 inside the cavity 200 of the stopper 2 leads to a load peak generated by the actuator 71. The maximum value of the load peak generated is measured, and retained as the snap-fastening force value.

For a syringe according to embodiments of the disclosure, the measured pull-out force may be between 11.8 N and 12.5 N, with a measured snap-fastening force of between 6.8 N and 8.6 N.

The disclosure is not limited to the disclosed embodiments. Anyone skilled in the art will be able to consider the technically workable combinations thereof, and to substitute equivalents therefor.

The invention claimed is:

1. A syringe comprising:

a syringe body for receiving a product for injection, the syringe body comprising a stopper, the stopper having an inner wall and delimiting a cavity, the inner wall being elastically deformable;

a piston mounted so as to be able to slide inside the syringe body in an injection direction of the product and in an other direction opposite to the injection direction of the product, the piston comprising a rod having a first end and a second end opposite the first end;

a pusher at the first end of the rod; and a snap-fastening head at the second end of the rod and snap-fastened inside the cavity of the stopper, the snap-fastening head having a planar bearing surface bearing against the inner wall of the stopper when the piston slides in the other direction that is opposite to the injection direction of the product;

wherein the snap-fastening head comprises at least one protruding element that protrudes from the planar bearing surface and that is arranged so as to penetrate the inner wall of the stopper when the piston slides in the other direction that is opposite to the injection direction of the product so that the at least one protruding element is anchored to the inner wall by locally deforming the inner wall;

wherein the planar bearing surface has a radius (R), and the at least one protruding element has a lateral end situated at a radial distance (r), such that: $0.8\,R \leq r \leq 1.20\,R$.

2. The syringe of claim 1, wherein the at least one protruding element comprises two planar surfaces forming an acute dihedral angle.

3. The syringe of claim 2, wherein the two planar surfaces of the at least one protruding element are joined together so as to form an edge.

4. The syringe of claim 1, wherein the at least one protruding element comprises a conical or frustoconical surface exhibiting an acute cone angle.

5. The syringe of claim 1, wherein the at least one protruding element forms a tooth exhibiting an acute tip angle.

6. The syringe of claim 1, wherein the planar bearing surface is situated at a distance (D) from the second end of the rod, and the at least one protruding element has a height (H) along the normal to the planar bearing surface, such that: $0.05\,D \leq H \leq 0.2\,D$.

7. The syringe of claim 1, wherein the at least one protruding element comprises a set of the protruding elements that protrude from the planar bearing surface and that are arranged so as to penetrate the inner wall of the stopper when the piston slides in the other direction that is opposite to the injection direction of the product.

8. The syringe of claim 7, wherein the protruding elements of the set form patterns that are spaced apart periodically on the planar bearing surface.

9. The syringe of claim 7, wherein the planar bearing surface is circular, and the set of the protruding elements is distributed uniformly around the planar bearing surface.

10. The syringe of claim 7, wherein the snap-fastening head extends along a longitudinal axis, and the protruding elements of the set exhibit axial symmetry with respect to the longitudinal axis.

11. The syringe of claim 1, wherein the at least one protruding element and the snap-fastening head are in one piece.

12. The syringe of claim 1, wherein the snap-fastening head and the at least one protruding element comprise a plastics material.

13. The syringe of claim 1, wherein the stopper comprises an elastomeric material.

14. The syringe of claim 1, wherein the inner wall of the stopper comprises at least one shoulder against which the planar bearing surface of the snap-fastening head bears when the piston slides in the other direction that is opposite to the injection direction of the product; and the at least one protruding element is arranged so as to penetrate the at least one shoulder when the piston slides in the other direction that is opposite to the injection direction of the product.

15. The syringe of claim 1, wherein the at least one protruding element:

comprises two planar surfaces forming an acute dihedral angle of between 10° and 80°, comprises a conical or frustoconical surface exhibiting an acute cone angle of between 10° and 80°, or forms a tooth exhibiting an acute tip angle of between 10° and 80°.

16. The syringe of claim 1, wherein the at least one protruding element:

comprises two planar surfaces forming an acute dihedral angle of between 30° and 60°, comprises a conical or frustoconical surface exhibiting an acute cone angle of between 30° and 60°, or forms a tooth exhibiting an acute tip angle of between 30° and 60°.

17. The syringe of claim 1, wherein the at least one protruding element:

comprises two planar surfaces forming an acute dihedral angle of between 40° and 50°, comprises a conical or frustoconical surface exhibiting an acute cone angle of between 40° and 50°, or forms a tooth exhibiting an acute tip angle of between 40° and 50°.

18. The syringe of claim 1, wherein:

the planar bearing surface is situated at a distance (D) from the second end of the rod, and the at least one protruding element has a height (H) along the normal to the planar bearing surface, such that $0.06\,D \leq H \leq 0.18\,D$; and/or the planar bearing surface has the radius (R), and the at least one protruding element has the lateral end situated at the radial distance (r), such that $R \leq r \leq 1.16\,R$.

19. The syringe of claim 1, wherein:

the snap-fastening head and the at least one protruding element comprise polycarbonate; and/or the stopper comprises chlorinated or brominated butyl rubber.

* * * * *